(12) United States Patent
Kieffer et al.

(10) Patent No.: US 10,259,767 B2
(45) Date of Patent: Apr. 16, 2019

(54) METHOD FOR THE PREPARATION OF ALKYLSALICYLALDEHYDE AND ALKYLSALICYLALDOXIME, AND USE THEREOF

(71) Applicant: S.P.C.M. SA, Andrezieux Boultheon (FR)

(72) Inventors: Johann Kieffer, Hopital le Grand (FR); Cédrick Favero, Saint Romain le Puy (FR)

(73) Assignee: S.P.C.M. SA, Andrezieux Boutheon (FR)

( * ) Notice: Subject to any disclaimer, the term of this patent is extended or adjusted under 35 U.S.C. 154(b) by 0 days.

(21) Appl. No.: 15/740,245

(22) PCT Filed: May 30, 2016

(86) PCT No.: PCT/EP2016/062143
§ 371 (c)(1),
(2) Date: Dec. 27, 2017

(87) PCT Pub. No.: WO2017/012757
PCT Pub. Date: Jan. 26, 2017

(65) Prior Publication Data
US 2018/0186714 A1    Jul. 5, 2018

(30) Foreign Application Priority Data

Jul. 23, 2015   (EP) ..................... 15178054

(51) Int. Cl.
| | |
|---|---|
| *C22B 3/16* | (2006.01) |
| *C07C 45/75* | (2006.01) |
| *C22B 15/00* | (2006.01) |
| *C07C 249/08* | (2006.01) |
| *C07C 251/48* | (2006.01) |
| *C07C 47/565* | (2006.01) |

(52) U.S. Cl.
CPC ............ *C07C 45/75* (2013.01); *C07C 47/565* (2013.01); *C07C 249/08* (2013.01); *C07C 251/48* (2013.01); *C22B 3/1633* (2013.01); *C22B 15/0065* (2013.01)

(58) Field of Classification Search
None
See application file for complete search history.

(56) References Cited

U.S. PATENT DOCUMENTS

| | | |
|---|---|---|
| 4,231,888 A | 11/1980 | Dalton |
| 4,351,962 A | 9/1982 | Gradeff et al. |
| 4,638,096 A * | 1/1987 | Virnig ................. C07C 45/68 502/171 |
| 5,399,761 A | 3/1995 | Levin |
| 5,849,172 A | 12/1998 | Allen et al. |
| 2001/0055553 A1 | 12/2001 | Kang et al. |

FOREIGN PATENT DOCUMENTS

| | | | |
|---|---|---|---|
| CN | 103539743 | * | 1/2014 |
| EP | 0106653 A2 | | 4/1984 |
| WO | 2007/034501 A2 | | 3/2007 |

OTHER PUBLICATIONS

Schall (Arenecarbaldehydes: Synthesis by Formylation of Arene-Hydrogen Bonds Science of Synthesis, vol. 25, 2007, p. 605-653) (Year: 2007).*
2,2,4-Trimethylpentane (Sigma-Aldrich Specification Sheet for 2,2,4-trimethylpentane/isooctane, downloaded from https://www.sigmaaldrich.com/catalog/product/sial/360066?lang=en&region=US on May 16, 2018, p. 1-4) (Year: 2018).*
International Search Report and Written Opinion of the International Searching Authority for PCT/EP2016/062143 dated Aug. 19, 2016.
Maki, T., et al., "Recent Progress in Manufacturing Technology for Aromatic Aldehydes", pp. 195-204, Abstract Only in English (1991).
Aldred, R., et al., "Magnesium-mediated ortho-specific formylation and formaldoximation of phenols", *Journal of the Chemical Society*, Perkins Transactions 1, Issue 13, Abstract Only (1994).

* cited by examiner

*Primary Examiner* — Amy C Bonaparte
(74) *Attorney, Agent, or Firm* — Heslin Rothenberg Farley & Mesiti P.C.

(57) ABSTRACT

The invention relates to an improved method for the preparation of alkylsalicylaldehyde or its corresponding metallic salts. The invention also relates to a method for the preparation of alkylsalicylaldoxime by reacting said alkylsalicylaldehyde or its corresponding metallic salts with hydroxylamine or its salt. The invention also relates to a method for extracting a metal in an aqueous solution containing dissolved metal.

17 Claims, No Drawings

METHOD FOR THE PREPARATION OF ALKYLSALICYLALDEHYDE AND ALKYLSALICYLALDOXIME, AND USE THEREOF

CROSS REFERENCE TO RELATED APPLICATIONS

This application is a national stage filing under section 371 of International Application No. PCT/EP2016/062143, filed on May 30, 2016, and published on Jan. 26, 2017 as WO 2017/012757, which claims priority to European Application No. 15178054.1, filed on Jul. 23, 2015. The entire contents of each of said applications are hereby incorporated herein by reference.

FIELD OF TECHNOLOGY

The present invention relates to an improved method for the preparation of alkylsalicylaldehyde or its corresponding metallic salts. The invention also relates to a method for the preparation of alkylsalicylaldoxime by reacting said alkylsalicylaldehyde or its corresponding metallic salts with hydroxylamine. The invention also relates to a method for extracting a metal in an aqueous solution containing dissolved valuable metal.

BACKGROUND OF THE INVENTION

Alkylsalicylaldehydes have so far been synthesised according to the Reimer Tiermann reaction but this process has important drawbacks: low yield and use of chloroform. Document «New progress in aromatic aldehyde production technology» published in «Journal of Synthetic Organic Chemistry, 1991, 49(3): 195-204» describes this reaction in details.

Another route has been described in document U.S. Pat. No. 4,351,962 by reaction of alkylphenol with boronic acid as an intermediate followed by formaldehyde addition. The alcohol intermediate formed is further oxidised by molecular oxygen in the presence of a platinum or palladium catalyst. However, this process is complex and the required conditions are harsh.

Document U.S. Pat. No. 5,399,761 describes an improved synthesis by reacting a phenolic compound and formaldehyde. The synthesis reaction is called formylation of phenols. More specifically, this document describes the oximation of 2-hydroxyarylsalicylaldehyde. The 2-hydroxyarylsalicylaldehyde is synthesised by formylation of magnesium bis-nonylphenoxide. The solvent used is toluene or xylene.

The document "Magnesium-mediated ortho-Specific Formylation and Formaldoximation of phenols" (Aldred et al., J. Chem. Soc. Perkin Trans., 1, 1994, 1823-1831) describes in details the formylation reaction of phenol derivatives with magnesium methoxide to produce the corresponding salicylaldehyde derivatives, and the oximation of said salicylaldehyde derivatives to produce the corresponding salicylaldoxime derivatives. Methanol and toluene are the typical solvent used during the synthesis reaction.

Document WO 2007/034501 discloses a new process for the manufacture of 5-nonylsalycylaldoxime in a two steps reaction involving a novel catalyst mixture comprising magnesium methoxide. Typically, the solvent used in this reaction is toluene.

Despite great advance in the formylation process, there is still a need to improve the process related to the preparation of alkylsalicylaldehyde or its corresponding metallic salts, especially with respect to:
an improved yield; and
an improved productivity by reducing the synthesis reaction time.

SUMMARY OF THE INVENTION

It has now been found that it is possible to achieve the above objectives (improved yield and productivity) by using specific solvents during the synthesis reaction.

Accordingly, in a first aspect, the present invention provides a method for the preparation of alkylsalicylaldehyde of formula (I) or its corresponding metallic salts of formula (II)

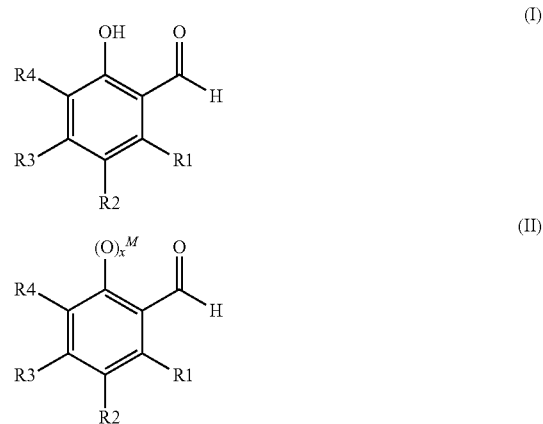

which comprises the following step:
a/ reacting a phenolic compound of formula (III)

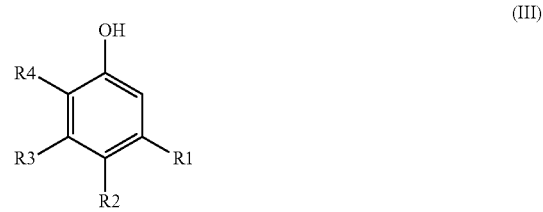

with formaldehyde or a formaldehyde liberating compound, in the presence of:
a solvent; and
a metal based reactant;
wherein each of R1, R2, R3, independently, are selected from the group comprising hydrogen; halogen atom; hydroxy group; C6-C12 alkyl group; C6-C12 cycloalkyl group; C6-C12 alkoxyl group; C6-C12 acyl group; C6-C12 aryl group; C6-C12 araryl group; C6-C12 alkaryl group; OR5 wherein R5 is a C1-C22 linear or branched alkyl group; C2-C22 linear or branched alkenyl group; a C6 aryl group; and C7-C22 aralkyl group;
wherein R4 is selected from the group comprising hydrogen atom; C1-C22 linear or branched alkyl group; C2-C22 linear or branched alkenyl group; C6 aryl group; C7-C22 aralkyl group; OH; OR5 wherein R5 is a C1-C22 linear or branched alkyl group;

C2-C22 linear or branched alkenyl group; C6 aryl group; and C7-C22 aralkyl group wherein M is a metal;

wherein x is a whole number from 1 to 4;

characterised in that the solvent is at least one C6-C14 alkane.

An alkane may be linear, branched or cyclic.

The solvent may be a $C_nH_{2n+2}$ alkane, in which n is a whole number from 6 to 14 or a C6-C14 cyclic alkane.

Cyclic alkanes include hydrocarbon compounds having one or more rings of carbon atoms. They correspond to formula $C_nH_{2(n+1-g)}$ wherein n is a whole number from 6 to 14 and g is the number of rings in the molecule.

The choice of the nature of the solvent is essential to the invention. It has been found that the selection of a specific solvent system improves the yield of the reaction and improves the productivity by reducing the synthesis reaction time.

The reaction is conducted in a solvent system comprising at least one alkane comprising 6 to 14 carbon atoms. The solvent system preferably comprises at least 50% in weight, more preferably at least 80% by weight, and even more preferably at least 95% by weight of at least a C6-C14 alkane.

The solvent system may either consist of one or a mixture of C6-C14 alkanes, preferably a C7 to C13 alkane.

The solvent is advantageously a $C_nH_{2n+2}$ linear or branched alkane, in which n is from 7 to 13. The solvent system may also be a C7-C13 cyclic alkane such as naphtene.

In a preferred embodiment, the solvent is selected from the group consisting of heptane, octane, nonane, decane, undecane, dodecane, tridecane, their isomers, and mixture thereof.

In another preferred embodiment, the solvent is nonane, or a mixture of C7 to C13 alkane.

The solvent system contains substantially no aromatic Volatile Organic Compound (VOC) such as benzene, toluene, xylene, ethyl benzene, styrene, chloro-benzene, 1,2 dichlorobenzene, 1,3 dichlorobenzene, 1,4 dichlorobenzene, benzyl chloride, benzyl bromide. In other words, the aromatic VOC may be present but at a "trace" level, generally below 5.000 ppm, preferably below 1.000 ppm.

In the method for the preparation of alkylsalicylaldehyde (formula I or II) of the invention, any phenolic of formula (III) may be used.

However, the phenolic compound is preferably selected from formula (III) wherein R1=R3=H, R2=C9-C12 alkyl, and R4=H or $CH_3$.

According to a preferred embodiment, the phenolic compound is selected from any of formula (IV) and (V) or a mixture thereof:

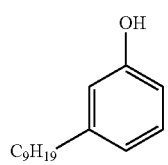

(IV)

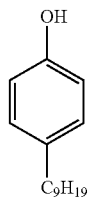

(V)

In the method for the preparation of alkylsalicylaldehyde of the invention any formaldehyde or formaldehyde liberating compound may be used for the preparation of alkylsalicylaldehyde of formula (I) or (II). The formaldehyde may be in the form of free gaseous formaldehyde or a solution in an anhydrous solvent or a formaldehyde-liberating compound.

A "formaldehyde-liberating compound" refers to a compound capable of liberating formaldehyde under the experimental conditions of the method according to the invention. Suitable formaldehyde-liberating compounds include polymeric forms of formaldehyde such as paraformaldehyde.

Formaldehyde and paraformaldehyde are preferably used.

In the method for the preparation of alkylsalicylaldehyde of the invention, the molar ratio between formaldehyde (or a formaldehyde liberating compound) and the phenolic compound of formula (III) is preferably from 2 to 5, more preferably from 2.25 to 3.25.

In a preferred embodiment the metal based reactant is a magnesium reactant. More preferably the metal based reactant is a compound of formula (VI), $Mg(OR6)_2$ wherein R6 is an alkyl group.

$$R6-O-Mg-O-R6 \quad (VI)$$

In a very preferred embodiment, the metal based reactant is a compound of formula (VI) wherein R6 is CH3.

It has been found that particularly advantageous results in terms of yield and reduced reaction time are obtained when a magnesium reactant is used in conjunction with an alkane comprising 6 to 14 atoms of carbon as solvent.

The preferred magnesium reactant is magnesium methoxide, $Mg(OMe)_2$.

When step a/ is started the molar ratio between the metal based reactant and the phenolic compound (III) is preferably from 0.3 to 3, more preferably from 0.4 to 1, and even more preferably from 0.5 to 0.7.

Optionally, a catalyst may be used in step a) of the method of the invention. Preferably, the catalyst is a compound of a metal $M_1$ of any of Group II, Group III, Group IV A or Group VI A of the Periodic Table.

For instance, suitable titanium or zirconium catalysts include compounds of formula (VII):

$$W-\underset{\underset{Z}{|}}{\overset{\overset{X}{|}}{M_1}}-Y \quad (VII)$$

wherein $M_1$ represents titanium or zirconium, and wherein each of W, X, Y and Z, independently, are selected from the group comprising halogen atom; alkoxy; aryloxy; alkaryloxy; aralkoxy; acyloxy; cyclopentadienyl group; a residue of a beta-diketone; a hydroxyquinoline; hydroxybenzaldehyde; and substituted 2-hydroxybenzaldehyde.

According to a particular embodiment, two of W, X, Y and Z together are an oxygen atom, each of the remaining two among W, X, Y and Z, independently, are selected from the group comprising halogen atom; alkoxy; aryloxy; aralkoxy; alkaryloxy; acyloxy group; a residue of a beta-diketone; a hydroxyquinoline; 2-hydroxybenzaldehyde; and substituted 2-hydroxybenzaldehyde.

Generally, the alkyl or acyl part of a group W, X, Y or Z contains up to 22 carbon atoms and the aryl part is preferably a phenyl group.

Specific examples of titanium based catalysts include titanium tetraisopropoxide, titanium tetrabutoxide, titanium cresylate and titanium tetraphenoxide.

Other suitable catalysts are $I_2$ and $HgCl_2$.

A suitable amount of catalyst is such that the molar ratio between the catalyst and the phenolic compound (III) is from 0.0005 to 0.017, more preferably from 0.0005 to 0.005.

During the reaction of step a/, alcohol is generated when the metal based reactant is of formula (VI) (for instance methanol is generated when $Mg(OMe)_2$ is used). According a particular embodiment, the yield may be maximised and the reaction time minimised by removing continuously the resulting alcohol so as to maintain the weight ratio alkane/the sum of alkylsalicylaldehyde of formula (I) or (II) and phenolic compound at the optimum level.

In a preferred embodiment, in step a/, the weight ratio alkane and the sum of alkylsalicylaldehyde of formula (I) or (II) and phenolic compound is continuously maintained between 0.5 and 10 during the reaction, more preferably 0.7 and 3.

The method for the preparation of alkylsalicylaldehyde of the invention is preferably carried out at a pressure comprised between 100 mbar (10 000 Pa) and 20 bar (2 000 000 Pa), preferably at a pressure comprised between 300 mbar (30 000 Pa) and the atmospheric pressure.

The method for the preparation of alkylsalicylaldehyde of the invention is preferably carried out at a temperature comprised between 40° C. and 140° C., preferably at a temperature comprised between 50° C. and 120° C.

As already mentioned, the method according to the first aspect of the invention leads to the formation of an alkylsalicylaldehyde of formula (I) or its corresponding metallic salts of formula (II).

For instance, when a magnesium methoxide is used as metal based reactant, the corresponding metallic salt of the alkylsalicylaldehyde is an organometallic complex of the aldehyde of formula (II-Mg).

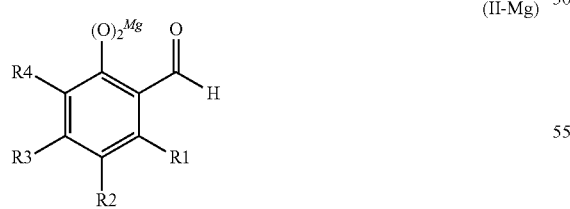

(II-Mg)

It is common general knowledge to add an acid to a metallic complex such as formula (II or II-Mg) in order to obtain the corresponding alkylsalicylaldehyde. Any type of organic or inorganic acid may be used but sulphuric acid is generally preferred.

Accordingly, the method of the first aspect of the invention may also comprise the step of adding an acid to the corresponding metallic salt of the aldehyde of formula (II).

In that case, sulphuric acid is preferably used as source of acid in a molar ratio acid:metal M content in the metal based reactant between 0.01:1 and 3:1, preferably between 0.2:1 and 1.5:1.

In a preferred embodiment, the formylation reaction (step a/), is carried out without the substantial presence of any aromatic Volatile Organic Compound (VOC) such as benzene, toluene, xylene, ethyl benzene, styrene, chloro-benzene, 1,2 dichlorobenzene, 1,3 dichlorobenzene, 1,4 dichlorobenzene, benzyl chloride, benzyl bromide. In other words, the aromatic VOC may be present but at a "trace" level, generally below 5.000 ppm, preferably below 1.000 ppm.

According to a particular embodiment, step a/ may be carried out in the presence of an activator.

In a second aspect, the present invention provides a method for the preparation of alkylsalicylaldoxime by oximation of the alkylsalicylaldehyde of formula (I) or its corresponding metallic salt of formula (II). The present invention also provides a method for the preparation of alkylsalicylaldoxime of formula (VIII) or its corresponding metallic salt of formula (IX):

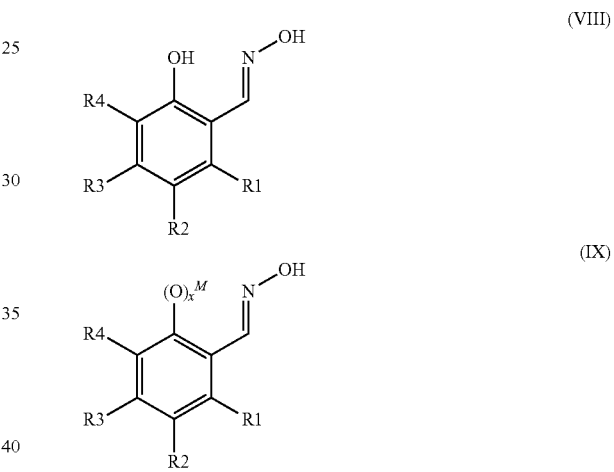

which comprises the following steps:
a/ preparation of an alkylsalicylaldehyde of formula (I) or its corresponding metallic salt of formula (II) according to the above described step a/, by reaction between a compound of formula (III) with formaldehyde or a formaldehyde liberating compound in the presence of a metal based reactant and a C6-C14 alkane solvent;
b/ reacting the resulting alkylsalicylaldehyde of formula (I) or its corresponding metallic salt of formula (II) with hydroxylamine or a salt of hydroxylamine.

R1, R2, R3 and R4 are as above defined.

The preferred metal based reactant of step a/ is a magnesium based reactant as described above.

The reaction of step b/ between the alkylsalicylaldehyde of formula (I) or its corresponding metallic salts (II) with hydroxylamine or a salt thereof is generally called an oximation reaction. The salt of hydroxylamine may be hydroxylamine sulfate or hydroxylamine hydrochloride. While hydroxylamine is preferred for technical reasons because it improves the oximation reaction, for practical and safety reasons, the use of hydroxylamine salts and particularly hydroxylamine sulfate is recommended. Hydroxylamine free base may be generated by pH adjustment.

Optionally, a catalyst as described above may be used in the step a/ of the method of the invention.

In a first alternative, step b/ of the reaction is carried out between the alkylsalicylaldehyde of formula (I) and hydroxylamine or a salt thereof.

In a second alternative, step b/ of the reaction is made between the corresponding metallic salts (II) of the alkylsalicylaldehyde of formula (I) and hydroxylamine or a salt thereof. In this alternative, the oximation reaction leads to an organometallic complex of the alkylsalicylaldoxime corresponding to formula (IX). In that case, the method comprises an additional step which consists of adding an acid to said complex in order to obtain the alkylsalicylaldoxime. This second alternative is not the preferred one.

The first alternative is preferred. In this preferred embodiment, the oximation is carried out on the alkylsalicylaldehyde of formula (I). It is possible to purify the alkylsalicylaldehyde resulting from step a/ before it reacts with the hydroxylamine, for example with a thin film evaporator or short path evaporator. It is also possible to purify the alkylsalicylaldehyde resulting from step a/ by water washing. It is also possible not to purify the alkylsalicylaldehyde resulting from step a/ before it reacts with hydroxylamine.

Purification of alkylsalicylaldehyde by evaporation leads to the formation of alkylphenolic-formaldehyde resins. The same is considered as an impurity and is detrimental to the performance of the resulting alkylsalicylaldehyde and thereof to the performance of the final alkylsalicylaldoxime in a metal solvent extraction process.

Even if it is not the object of the invention, it has been found a secondary advantage of the method for the preparation of alkylsalicylaldoxime of the invention. The quality of the alkylsalicylaldehyde (I or II) obtained by the method of the invention is such that it is possible to obtain a satisfactory quality of alkylsalicylaldoxime of formula (VIII) or its corresponding metallic salts of formula (IX) without requiring any purification of the alkylsalicylaldehyde of formula (I) or (II) resulting from step a/.

In other words, it means that a satisfactory quality of alkylsalicylaldoxime (VIII or IX) may be obtained by reacting the alkylsalicylaldehyde of formula (I) or (II) directly obtained by the method of the first aspect of the invention, without requiring any purification of said aldehyde before it reacts with the hydroxylamine or its salt.

In a preferred embodiment of the second aspect of the invention (steps a/+b/), the alkylsalicylaldehyde of formula (I) or (II) obtained according to the method of the first aspect of the invention (step a/), is substantially non purified before reacting with hydroxylamine or a salt thereof according to step b/.

It is also preferable to carry out the preparation of alkylsalicylaldoxime of the invention (step b/) in the presence of an inert solvent so as to limit the temperature exposure of the alkylsalicylaldoxime of the invention.

An "inert solvent" refers to a solvent that does not react with any compound of the reaction.

Inert solvents suitable for step b/ include hydrocarbon solvents; linear, cyclic, or branched alkanes and their isomers; trimethyl pentanyl diisobutyrate (for instance TXIB™ trademark of Eastman company); tridecylalcohol (for instance Exxal™ 13 trademark of Exxon Mobil Chemical company); and mixtures thereof.

In a preferred embodiment, the oximation reaction of step b/ is conducted without the substantial presence of any aromatic Volatile Organic Compound (VOC) such as benzene, toluene, xylene, ethyl benzene, styrene, chloro-benzene, 1,2 dichlorobenzene, 1,3 dichlorobenzene, 1,4 dichlorobenzene, benzyl chloride, benzyl bromide. In other words, the aromatic VOC may be present but at a "trace" level, generally below 5.000 ppm, preferably below 1.000 ppm.

In the method for the preparation of alkylsalicylaldoxime (VIII or IX) of the invention, it is preferred that the molar ratio between the hydroxylamine (or its salt) in free form and the alkylsalicylaldehyde (I or II) ranges from 0.6 to 6, preferably from 0.8 to 2, more preferably from 1 to 1.4. For instance, the corresponding molar ratio between hydroxylamine sulfate and the alkylsalicylaldehyde (I or II) preferably ranges from 0.3 to 3, more preferably from 0.4 to 1, and even more preferably from 0.5 to 0.7.

The method for the preparation of alkylsalicylaldoxime of the invention is preferably carried out at a temperature comprised between 20° C. and 120° C., preferably at a temperature comprised between 30° C. and 90° C.

The alkylsalicylaldoxime of formula (VII) may be used in a metal recovery method.

Metals are generally obtained from its ore by a solvent extraction process as it is described in the documents U.S. Pat. Nos. 4,231,888 and 6,632,410.

The starting material for solvent extraction process is an aqueous leach solution obtained from a body of ore which contains a mixture of metals. The leaching medium dissolves salts of metals as it trickles through the ore, to provide an aqueous solution of the mixture of metal. The metal are usually leached with sulphuric acid medium, providing an acidic aqueous solution, but can also be leached by ammonia to provide a basic aqueous solution.

The aqueous solution is mixed with an extracting composition which comprises an extracting chemical which selectively forms a metal-extractant complex with the ions of the metal to be recovered, in preference to ions of other metals.

Alkylsalicylaldoxime compounds are generally good candidates as extracting chemicals.

The alkylsalicylaldoxime resulting from the method of the present invention (steps a/+b/) may be provided as a composition for use in separating selectively a metal in an aqueous solution containing dissolved metals in a metal extracting process. Said composition comprises at least one alkylsalicylaldoxime of formula (VIII).

The amount of alkylsalicylaldoxime contained in the metal extracting composition is generally between 0.1 to 90 weight % of alkylsalicylaldoxime, preferably between 20 and 60 w %, as compared to the weight of the composition.

The composition may be used in a metal extraction process of any metal capable of forming a lipophilic complex with the alkylsalicylaldoxime, for example cobalt, nickel, zinc, cadmium, silver, and preferably copper.

It has also been found that it is also possible to obtain a satisfactory quality of alkylsalicylaldoxime by reacting the alkylsalicylaldehyde obtained by the method of the first aspect of the invention with hydroxylamine or a salt thereof, without it being necessary to purify said aldoxime before its use as a metal extractant reagent.

The metal extracting composition can therefore contain an alkylsalicylaldoxime which is substantially non purified after being directly obtained by the method according to the second aspect of the invention.

Even if it is not the object of the invention, it has also been found that it is also possible to obtain a satisfactory quality of alkylsalicylaldoxime by reacting the alkylsalicylaldehyde obtained by the method of the first aspect of the invention with hydroxylamine or a salt thereof, without it being necessary to purify said aldehyde before it reacts with the hydroxylamine, and without it being necessary to purify said alkylsalicylaldoxime before its use as a metal extractant reagent.

In a particular embodiment, the metal extracting composition contains an alkylsalicylaldoxime which is directly obtained by the method of the second aspect of the invention, wherein the alkylsalicylaldehyde is substantially non purified before reacting with hydroxylamine, and wherein the alkylsalicylaldoxime is substantially non purified after being directly obtained by the method according to the second aspect of the invention.

The metal extracting composition is generally made by mixing at least one alkylsalicylaldoxime of formula (VIII) with a water-immiscible organic solvent. Typical solvent are hydrocarbon solvent, linear, cyclic or branched alkane and the isomers of said alkane, trimethyl pentanyl diisobutyrate (for instance TXIB™ trademark of Eastman company), tridecylalcohol (for instance Exxal™ 13 trademark of Exxon Mobil Chemical company), and mixtures thereof.

The metal extracting composition may also comprise other components such as any one of the following: surfactant, transfer agent, ligands, conditioners, alkylphenols or ketoximes such as 2-hydroxy-5-alkyl-arylketoxime.

The invention also provides a method for extracting a metal $M_2$ from an aqueous solution containing dissolved metal $M_2$. This method comprises the following steps:

a/ preparation of a compound of formula (I) or (II) as above described;
b/ preparation of a compound of formula (VIII) as above described;
c/ contacting an aqueous solution containing a metal $M_2$ with a composition comprising the compound of formula (VIII) resulting from step b/.

The method for the extraction of a metal $M_2$ comprises step c/, which consists in contacting an aqueous solution containing dissolved metal $M_2$ with the above metal extracting composition according, to form an aqueous phase and an organic phase comprising a metal-extractant complex.

In a preferred embodiment, in step c/, the composition is a water-immiscible organic solution comprising the compound of formula (VIII) and a hydrocarbon solvent. Step c/ therefore results in the formation of:
an aqueous phase; and
an organic phase comprising a hydrocarbon solvent and a metal-extractant complex.

Generally, the method further comprises additional step d/ that consists in separating said organic phase from the aqueous phase and recovering the metal $M_2$ from the organic phase, generally by electrowinning process such as described in the document U.S. Pat. No. 5,849,172.

The amount of alkylsalicylaldoxime used in the method depends upon the concentration of metal $M_2$ in the aqueous solution and the plant configuration. This amount is generally comprised between 5 and 200 g of alkylsalicylaldoxime per liter of organic phase comprising metal-extractant complex.

The method for extracting a metal $M_2$ is particularly suitable for extracting copper from its ore, and especially from iron comprised in the leach solution obtained from its ore. It has been found that the metal extracting composition of the invention is particularly efficient in the process of extracting copper. The alkylsalicylaldoxime of formula (VIII) offers an excellent selectivity between copper and iron, especially when R1=R3=H, R2=C9-C12 alkyl group, and R4=H or $CH_3$. The method for extracting a metal $M_2$ is also particularly suitable for extracting cobalt from its ore.

As already mentioned, the formylation reaction in the first aspect of the invention is preferably conducted without the presence of aromatic hydrocarbon. This absence of aromatic hydrocarbon may lead to a metal extracting composition free of aromatic hydrocarbon when the oximation reaction is conducted without aromatic hydrocarbon, which is preferred, and when no additional aromatic hydrocarbon is added in the metal extracting composition.

An advantage of the invention is the reduction of hazardous compounds such as benzene or toluene and the improvement of working conditions during metal extracting process.

The skilled man of the art knows how to conduct a method of extracting a metal. Those processes are described for example in the documents U.S. Pat. Nos. 4,231,888 and 6,632,410 which are incorporated herein.

The choice of the nature of the solvent in which the formylation reaction is conducted is essential to the invention. The specific selection of solvent improves the yield of the reaction and improves the productivity by reducing the synthesis reaction time all other conditions being equal.

The following examples are meant to illustrate the invention without limiting its scope.

EXAMPLES

Example 1

Invention

A 1 liter glass reactor fitted with a temperature probe, a condenser and a stirring system is charged with 111.2 g of nonane, 50 g of methanol (1.56 mol), and 6.7 g of magnesium chips (0.28 mol). An activator solution, 7.4 ml of magnesium methoxide 7%, is added to activate the magnesium, and the mixture is heated to reflux temperature during 1 hour.

After magnesium dissolution, the mixture is further heated under reflux during 1 h to ensure reaction completion; reaction end-point is observed when hydrogen gas production has ceased. This reaction affords magnesium methoxide, which is thereafter used as metal based reactant.

100 g of para-nonyl phenol (0.45 mol) is added to the resulting magnesium methoxide and the mixture is maintained under reflux for 0.5 hour to achieve formation of magnesium bis-nonylphenoxide.

The condenser is then changed by a distillation head, and methanol/nonane azeotrope is evaporated during 1 hour until the mixture temperature reached 80° C. 58.4 g of distillate is obtained; it contains 90% of methanol by weight.

The mixture is heated to 85° C. and 41 g of paraformaldehyde (1.36 mol) is added by portion over a period of 1 hour, with continuous removal of volatile product distillate. On completion of paraformaldehyde addition, the mixture is heated at 95° C. during 1 hour to ensure completion of reaction.

The mixture is then cooled to approximately 50° C. A solution of 130 g of a 22% $H_2SO_4$ aqueous solution (0.29 mol) is added on top of the reaction mixture during 20 minutes.

The aqueous layer (pH<1) is discarded while the organic layer is further washed 2 times with 100 g of fresh water during 20 minutes for each washing.

The resulting organic layer is subjected to evaporation under vacuum with a wiped film evaporator to remove the nonane solvent. 106 g of crude nonylsalicylaldehyde is obtained, yield is 92%. The resulting nonylsalicylaldehyde is free of any aromatics and the residual nonane solvent amounts to less than 0.1% by weight.

The total batch cycle time is 6.5 hours.

Example 2

Counter-example

A 1 liter glass reactor fitted with a temperature probe, a condenser and a stirring system is charged with 175.9 g of toluene, 57.6 g of methanol (1.79 mol) and 6.7 g of magnesium chips (0.28 mol). An activator solution, 7.4 ml of magnesium methoxide 7%, is added to activate the magnesium, and the mixture is heated to reflux temperature during 1 hour.

After magnesium dissolution, the mixture is further heated under reflux during 1 hour to ensure reaction completion; reaction end-point is observed when hydrogen gas production has ceased.

100 g of para-nonyl phenol (0.45 mol) is added and the mixture is maintained under reflux for 0.5 hour to achieve formation of magnesium bis-nonylphenoxide.

The condenser is then substituted by a distillation head, and methanol/toluene azeotrope is evaporated during 2 hours until the mixture temperature reached 80° C. 84 g of distillate is obtained; it contains 69% of methanol by weight.

The resulting mixture is heated to 90° C. and 41 g of paraformaldehyde (1.36 mol) is added by portion over a period of 3 hours, with continuous removal of volatile product distillate. On completion of paraformaldehyde addition, the mixture is heated at 95° C. during 1 hour to ensure completion of the reaction.

The mixture is then cooled to approximately 50° C. A solution of 130 g of a 22% $H_2SO_4$ aqueous solution (0.29 mol) is added on top of the reaction mixture during 20 minutes.

The aqueous layer (pH<1) is discarded while the organic layer is further washed 2 times with 100 g of fresh water during 20 minutes for each washing.

The resulting organic layer is subjected to evaporation under vacuum with a wiped film evaporator to remove the toluene solvent. 102 g of crude nonylsalicylaldehyde is obtained. Yield is 90%. The resulting nonylsalicylaldehyde contains 1% of toluene.

The total batch cycle time is 9.5 hours.

Example 3

Oximation Process 68 g of nonylsalicyladehyde (0.27 mol) obtained according to example 1, 55.5 g of water (3.03 mol), 23.5 g of 50% a caustic (NaOH) solution (0.29 mol), 12.7 g of Escaid™ 110 (C7-C13 hydrocarbon fluid, trademark of ExxonMobil) 110, 26.9 g of trimethyl pentanyl diisobutyrate (TXIB™ trademark of Eastman company) and 23.4 g of hydroxylamine sulfate (0.14 mol) are mixed in a 4 neck round flask. The mixture is heated at 65° C. and stirred until nonylsalicylaldehyde is converted to the corresponding nonylsalicylaldoxime (indicated by FTIR by disappearance of the CH=O band at 1655 cm$^{-1}$).

The mixture is settled and the aqueous phase is discarded. The organic phase is washed with 80 g of a 6% sulfuric acid aqueous solution.

The organic layer is further washed 2 times with 80 g of fresh water.

The resulting organic solution is dried over sodium sulphate. The desired product nonylsalicylaldoxime is obtained as a pale yellow oil.

The invention claimed is:

1. A process for the preparation of an alkylsalicylaldehyde of formula (I) or its corresponding metallic salts of formula (II)

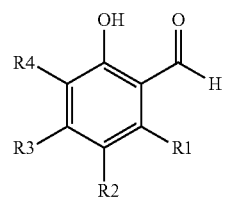

(I)

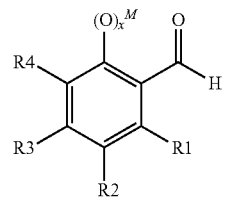

(II)

which comprises the following step:
a/ reacting a phenolic compound of formula (III)

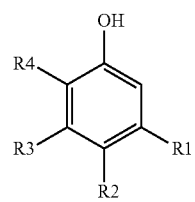

(III)

with formaldehyde or a formaldehyde liberating compound, in the presence of:
  a solvent selected from the group consisting of heptane, octane, nonane, decane, undecane, dodecane, tridecane, their isomers, and mixtures thereof; and
  a magnesium based reactant;
wherein each of R1, R2 and R3, independently, are selected from the group consisting of hydrogen atom; halogen atom; hydroxy group; C6-C12 alkyl group; C6-C12 cycloalkyl group; C6-C12 alkoxyl group; C6-C12 acyl group; C6-C12 aryl group; C12 araryl group; C7-C12 alkaryl group; and OR5 wherein R5 is a C1-C22 linear or branched alkyl group, C2-C22 linear or branched alkenyl groups, C6 aryl group, or C7-C22 aralkyl group;
wherein R4 is selected from the group consisting of hydrogen atom; C1-C22 linear or branched alkyl group; C2-C22 linear or branched alkenyl group; C6 aryl group; C7-C22 aralkyl group; OH; and OR5 wherein R5 is a C1-C22 linear or branched alkyl group, C2-C22 linear or branched alkenyl group, C6 aryl group, or C7-C22 aralkyl group;
wherein M is magnesium; and
wherein x is 2.

2. The process according to claim 1, wherein the solvent is selected from the group consisting of heptane, octane, nonane, decane, undecane, dodecane, tridecane, and mixtures thereof.

3. The process according to claim 1, wherein the solvent is selected from the group consisting of nonane, decane, undecane, dodecane, tridecane, their isomers, and mixtures thereof.

4. The process according to claim 1, wherein, in the phenolic compound of formula (III), R1=R3=H, R2=C9-C12 alkyl, and R4=H or $CH_3$.

5. The process according to claim 1, wherein during step a/, the weight ratio between the alkane solvent and the sum of alkylsalicylaldehyde of formula (I) and (II) and phenolic compound of formula (III) is continuously maintained between 0.5 and 10.

6. The process according to claim 1, wherein, when step a/ is started, the molar ratio between the magnesium based reactant and the phenolic compound of formula (III) is from 0.3 to 3.

7. The process according to claim 1, wherein the molar ratio between formaldehyde or a formaldehyde liberating compound and the phenolic compound of formula (III) is from 2 to 5.

8. A process for the preparation of an alkylsalicylaldoxime of formula (VIII) or its corresponding metallic salts of formula (IX):

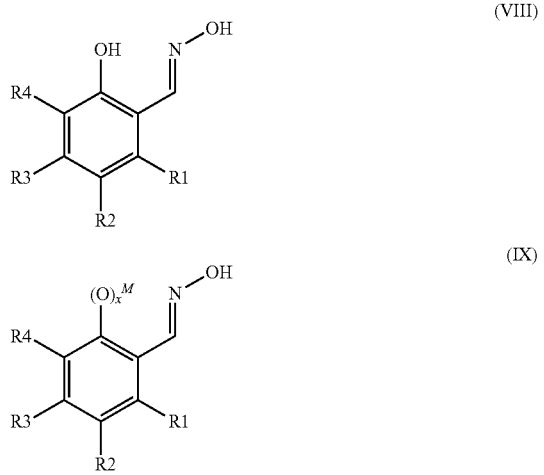

which comprises the following steps:

a/ preparing an alkylsalicylaldehyde of formula (I) or its corresponding metallic salts of formula (II)

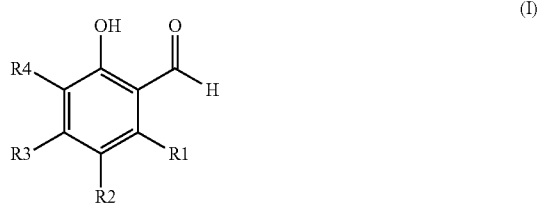

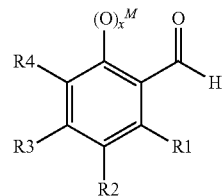

by reacting a phenolic compound of formula (III)

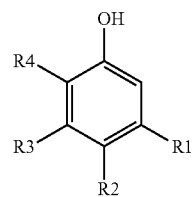

with formaldehyde or a formaldehyde liberating compound, in the presence of:
  a solvent selected from the group consisting of heptane, octane, nonane, decane, undecane, dodecane, tridecane, their isomers, and mixtures thereof; and
  a magnesium based reactant;
  wherein each of R1, R2, and R3, independently, are selected from the group consisting of hydrogen atom; halogen atom; hydroxy group; C6-C12 alkyl group; C6-C12 cycloalkyl group; C6-C12 alkoxyl group; C6-C12 acyl group; C6-C12 aryl group; C12 araryl group; C7-C12 alkaryl group; and OR5 wherein R5 is a C1-C22 linear or branched alkyl group, C2-C22 linear or branched alkenyl groups, C6 aryl group, or C7-C22 aralkyl group;
  wherein R4 is selected from the group consisting of hydrogen atom; C1-C22 linear or branched alkyl group; C2-C22 linear or branched alkenyl group;
  C6 aryl group; C7-C22 aralkyl group; OH; and OR5 wherein R5 is a C1-C22 linear or branched alkyl group, C2-C22 linear or branched alkenyl groups, C6 aryl groups, or C7-C22 aralkyl group;
  wherein M is magnesium; and
  wherein x is 2; and
b/ reacting the alkylsalicylaldehyde of formula (I) or its corresponding metallic salts of formula (II) resulting from step a/, with hydroxylamine or a salt of hydroxylamine.

9. The process according to claim 8, wherein step b/ is carried out between the alkylsalicylaldehyde of formula (I) and hydroxylamine or a salt of hydroxylamine.

10. The process according to claim 8, wherein the alkylsalicylaldehyde of formula (I) resulting from step a/ is substantially non purified before reacting with hydroxylamine or a salt of hydroxylamine during step b/.

11. A method for extracting a metal $M_2$ in an aqueous solution containing dissolved metal comprising the following steps:
  a/ preparing an alkylsalicylaldehyde of formula (I) or its corresponding metallic salts of formula (II)

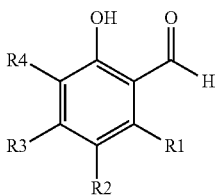

(I)

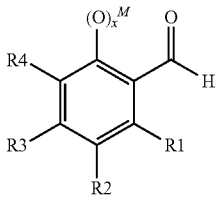

(II)

by reacting a phenolic compound of formula (III)

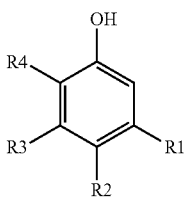

(III)

with formaldehyde or a formaldehyde liberating compound, in the presence of:
  a solvent selected from the group consisting of heptane, octane, nonane, decane, undecane, dodecane, tridecane, their isomers, and mixtures thereof; and
  a magnesium based reactant;
wherein each of R1, R2, and R3, independently, are selected from the group consisting of hydrogen atom; halogen atom; hydroxy group; C6-C12 alkyl group; C6-C12 cycloalkyl group; C6-C12 alkoxyl group; C6-C12 acyl group; C6-C12 aryl group; C12 araryl group; C7-C12 alkaryl group; and OR5 wherein R5 is a C1-C22 linear or branched alkyl group, C2-C22 linear or branched alkenyl group, C6 aryl group, or C7-C22 aralkyl group;
wherein R4 is selected from the group consisting of hydrogen atom; C1-C22 linear or branched alkyl group; C2-C22 linear or branched alkenyl group; C6 aryl group; C7-C22 aralkyl group; OH; and OR5 wherein R5 is a C1-C22 linear or branched alkyl group, C2-C22 linear or branched alkenyl group, C6 aryl group, or C7-C22 aralkyl group;
wherein M is magnesium; and
wherein x is 2;
b/ preparing an alkylsalicylaldoxime of formula (VIII):

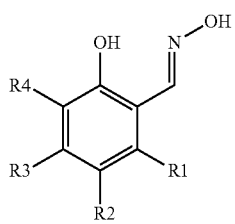

(VIII)

by reacting the alkylsalicylaldehyde of formula (I) or its corresponding metallic salts of formula (II) resulting from step a/, with hydroxylamine or a salt of hydroxylamine; and
c/ contacting an aqueous solution containing a metal $M_2$ with a composition comprising the compound of formula (VIII) resulting from step b/.

12. The process according to claim 11, wherein the composition comprising the compound of formula (VIII) is a water-immiscible organic solution comprising a hydrocarbon solvent.

13. The process according to claim 11, wherein the metal $M_2$ is copper.

14. The process according to claim 7, wherein the molar ratio between formaldehyde or a formaldehyde liberating compound and the phenolic compound of formula (III) is 2.25 to 3.25.

15. The process according to claim 3, wherein, in the phenolic compound of formula (III), R1=R3=H, R2=C9-C12 alkyl, and R4=H or $CH_3$.

16. The process according to claim 15, wherein during step a/, the weight ratio between the alkane solvent and the sum of alkylsalicylaldehyde of formula (I) and (II) and phenolic compound of formula (III) is continuously maintained between 0.5 and 10.

17. The process according to claim 15, wherein, when step a/ is started, the molar ratio between the magnesium based reactant and the phenolic compound of formula (III) is from 0.3 to 3.

* * * * *